United States Patent
Levy et al.

(10) Patent No.: US 11,918,832 B2
(45) Date of Patent: *Mar. 5, 2024

(54) SYSTEMS AND METHODS FOR SELECTIVE, TARGETED OPENING OF THE BLOOD-BRAIN BARRIER

(71) Applicant: INSIGHTEC, LTD., Tirat Carmel (IL)

(72) Inventors: Yoav Levy, Hinanit (IL); Eyal Zadicario, Tel-Aviv-Yafo (IL); Javier Grinfeld, Tell-Aviv-Yafo (IL); Rafi De Picciotto, Tirat Carmel (IL)

(73) Assignee: Insightec Ltd., Tirat Carmel (IL)

( * ) Notice: Subject to any disclaimer, the term of this patent is extended or adjusted under 35 U.S.C. 154(b) by 158 days.

This patent is subject to a terminal disclaimer.

(21) Appl. No.: 16/607,509

(22) PCT Filed: May 22, 2018

(86) PCT No.: PCT/IB2018/000774
§ 371 (c)(1),
(2) Date: Oct. 23, 2019

(87) PCT Pub. No.: WO2018/215839
PCT Pub. Date: Nov. 29, 2018

(65) Prior Publication Data
US 2020/0139158 A1 May 7, 2020

Related U.S. Application Data

(60) Provisional application No. 62/510,023, filed on May 23, 2017.

(51) Int. Cl.
*A61N 7/00* (2006.01)
*A61B 90/00* (2016.01)

(52) U.S. Cl.
CPC .............. *A61N 7/00* (2013.01); *A61B 90/37* (2016.02); *A61B 2090/374* (2016.02);
(Continued)

(58) Field of Classification Search
CPC ........ A61B 17/225; A61B 2017/00154; A61B 2017/22008; A61B 2018/00791;
(Continued)

(56) References Cited

U.S. PATENT DOCUMENTS

| | | | |
|---|---|---|---|
| 2008/0319356 A1 | 12/2008 | Cain et al. | |
| 2010/0318002 A1* | 12/2010 | Prus ................. | A61B 17/22004 601/2 |
| 2018/0085023 A1* | 3/2018 | Tillander ............... | A61B 5/055 |

FOREIGN PATENT DOCUMENTS

| | | | | |
|---|---|---|---|---|
| WO | 20060136912 A1 | 12/2006 | | |
| WO | WO-2006136912 A1 * | 12/2006 | ............. | A61B 8/467 |

(Continued)

OTHER PUBLICATIONS

Bbahark Sajjadi et al. "Influence of ultrasound power on acoustic streaming and micro-bubbles formations in a low frequency sonoreactor: Mathematical and 3D computational simulation," Sep. 27, 2014, Ultrasonics Sonochemistry, 24, pp. 193-203 (Year: 2014).*

(Continued)

*Primary Examiner* — Joseph M Santos Rodriguez
*Assistant Examiner* — Maria Christina Talty
(74) *Attorney, Agent, or Firm* — Morgan, Lewis & Bockius LLP

(57) ABSTRACT

Systems and methods for applying ultrasound sonication to temporarily disrupt a patient's blood-brain barrier (BBB) include storing threshold values of an acoustic response level, an acoustic response dose and a tissue response dose associated with a target BBB region and its surrounding regions based on anatomical characteristics thereof; causing the ultrasound transducer to transmit one or more pulses/waves; measuring the acoustic response level, the acoustic response dose, and/or the tissue response dose associated with the target BBB region and/or its surrounding regions; comparing the measurement with a corresponding stored threshold value; and operating the transducer based at least in part on the comparison.

27 Claims, 10 Drawing Sheets

(52) U.S. Cl.
CPC ............... *A61N 2007/0021* (2013.01); *A61N 2007/0039* (2013.01); *A61N 2007/0065* (2013.01)

(58) Field of Classification Search
CPC .... A61B 2018/00803; A61B 2090/374; A61B 2090/3762; A61B 2090/378; A61B 90/37; A61M 37/0092; A61N 2007/0021; A61N 2007/003; A61N 2007/0039; A61N 2007/0065; A61N 2007/0086; A61N 2007/0095; A61N 7/00
See application file for complete search history.

(56) References Cited

FOREIGN PATENT DOCUMENTS

| WO | 20080143998 | A1 | | 11/2008 | |
|---|---|---|---|---|---|
| WO | 20150187968 | A1 | | 12/2015 | |
| WO | WO-2015187968 | A1 | * | 12/2015 | ........ A61M 37/0092 |

OTHER PUBLICATIONS

Chih-Hung Tsai et al., "Real-time monitoring of focused ultrasound blood-brain barrier opening via subharmonic acoustic emission detection: implementation of confocal dual-frequency piezoelectric transducers," Mar. 17, 2016, Physics in Medicine & Biology, 61, pp. 2926-2946 (Year: 2016).*
Costas D. Arvanitis and Nathan McDonald, "Integrated ultrasound and magnetic resonance imaging for simultaneous temperature and cavitation monitoring during focused ultrasound therapies," Medical Physics, 40, 11, pp. 112901-1 to 112901-14 (Year: 2013).*
Yoshiki Yamakoshi et al., "Yeast Cell Trapping In Ultrasonic Wave Field Using Ultrasonic Contrast Agent," 2006, Japanese Journal of Applied Physics, 45, pp. 4712-4717 (Year: 2006).*
Alison Burgess et al., "Focused ultrasound-mediated drug delivery through the blood-brain barrier," May 2015, Expert Rev. Neurother. 15, 5, pp. 477-491 (Year: 2015).*
International Search Report and Written Opinion issued in a corresponding International Application No. PCT/IB2018/000774 dated Nov. 26, 2018.
First Office Action, CN2018800343421, dated Jun. 3, 2021, 16 pgs.
Notice of Allowance, CN2018800343421, dated Dec. 2, 2021, 2 pgs.

* cited by examiner

SYSTEMS AND METHODS FOR SELECTIVE, TARGETED OPENING OF THE BLOOD-BRAIN BARRIER

CROSS-REFERENCE TO RELATED APPLICATION

This application is a U.S. National Phase Application of PCT/IB2018/000774, filed May 22, 2018, which claims priority to, and the benefit of, U.S. Provisional Patent Application No. 62/510,023, filed on May 23, 2017. The foregoing applications are incorporated herein by reference in their entireties.

FIELD OF THE INVENTION

The field of the invention relates generally to ultrasound systems and, more particularly, to systems and methods for selective, targeted opening of the blood-brain barrier using an ultrasound procedure.

BACKGROUND

The blood-brain barrier (BBB), formed by layers of cells in the central nervous system (CNS), excludes large molecules from entering the brain parenchyma, thereby protecting it from damage by toxic foreign substances. But the BBB also presents one of the largest obstacles to treating many brain diseases. Specifically, the BBB prevents many therapeutic agents, such as drugs and gene-therapy vectors, from reaching a patient's brain tissue. For example, treatments for CNS infections, neurodegenerative diseases, congenital enzyme defects and brain cancer are all hampered by the ability of the BBB to block passage of, inter alia, antibiotics, anti-retroviral drugs, enzyme replacement therapy, gene preparations and anti-neoplastic drugs. It is thus desirable to temporarily and locally "open" the BBB to permit therapeutic quantities of these agents to access the affected brain tissue.

Focused ultrasound (i.e., acoustic waves having a frequency greater than about 20 kiloHertz) has been utilized to open the BBB in the treatment of neurological diseases. The mechanistic event underlying the BBB opening appears to involve the reaction of microbubbles to ultrasonic pulses, which can result in an array of behaviors known as acoustic cavitation. In stable cavitation, microbubbles expand and contract with the acoustic pressure rarefaction and compression over several cycles; such action can result in dilation and contraction of blood vessels in the vicinity. In inertial cavitation, the microbubbles can expand to several factors greater than their equilibrium radius and subsequently collapse due to the inertia of the surrounding tissue. In both cases, the consequent disruption of blood vessels induces "opening" of the BBB.

An uncontrolled microbubble cavitation, however, may result in undesired damage to and around the BBB. For example, ablating cells forming portions of the BBB may not only compromise BBB function but also cause unwanted cell death or necrosis in surrounding tissue. To minimize the undesired effects of microbubble cavitation during BBB disruption, one conventional approach utilizes a passive cavitation detector that measures the acoustic response of the microbubbles after each ultrasound sonication; if the acoustic response level is above a predefined threshold amplitude, the ultrasound procedure is suspended. The effects of microbubble cavitation, however, may be cumulative along a sonication and over a series of sonications, and may also depend on the properties of the tissue where cavitation occurs—that is, measuring the acoustic response from the microbubbles may not accurately reflect the effect of cavitation on the surrounding tissue.

Accordingly, there is a need to reliably detect microbubble cavitation resulting from ultrasound waves and monitor effects of the cavitation on the local tissue in real time so as to avoid permanent damage to the BBB or its surrounding tissue.

SUMMARY

The present invention provides systems and methods for inducing microbubble cavitation with ultrasound in order to disrupt a target BBB region in a controlled and reversible manner. The formation and cumulative amount of microbubble cavitation may be reliably detected using (i) an acoustic response level that represents a temporal acoustic effect of the microbubbles after each ultrasound sonication pulse and (ii) an acoustic response dose that represents a cumulative effect of the microbubbles over a single sonication or multiple sonications. For example, the acoustic response dose may be an integral of the time-varying acoustic response level over a predetermined time period. Therefore, if the detected acoustic response level and/or cumulative acoustic response dose exceeds a predetermined threshold reflecting an upper limit on the magnitude and/or cumulative amount of microbubble cavitation that can clinically tolerated—e.g., that does not permanently affect or damage the target BBB region or its surrounding tissue—the ultrasound procedure may be suspended to avoid further inducing microbubble cavitation. If, however, the detected acoustic response level and/or cumulative acoustic response dose is below the predetermined threshold, additional microbubble cavitation may be induced to further disrupt the target BBB region. This may be achieved by operating the ultrasound transducer to deliver additional acoustic energy to the target BBB region and/or activating a microbubble administration system to introduce additional microbubbles.

In some embodiments, an imaging device (e.g., a magnetic resonance imaging (MRI) device) is employed to characterize tissue types and/or properties of the target BBB region and/or its surrounding tissue; each type and location of tissue, depending on its properties, may have corresponding tolerances for the acoustic response level and acoustic response dose. In addition, the imaging device may measure the cavitation effects (e.g., a temperature increase or an area that is disrupted) on the target BBB region and/or the surrounding tissue in real time. If an undesired effect on the target BBB region and/or its surrounding tissue is observed (e.g., the temperature increase exceeding a threshold and/or a disrupted area larger than a desired size), the ultrasound procedure may be halted. Accordingly, approaches described in the current invention may advantageously avoid permanent damage of the target BBB region and its surrounding tissue by reliably detecting microbubble cavitation events and monitoring effects of the cavitation on the target and/or surrounding tissue in real time.

Accordingly, in a first aspect, the invention pertains to a system for temporarily disrupting a patient's blood-brain barrier (BBB). In various embodiments, the system includes an ultrasound transducer and a controller configured to (a) store one or more threshold values of an acoustic response level, a cumulative acoustic response dose and/or a tissue response dose associated with one or more target BBB regions and their surrounding regions; (b) cause the transducer to transmit one or more ultrasound pulses; (c) acquire the acoustic response level, the acoustic response dose, and/or the tissue response dose associated with the target BBB region(s) and/or the surrounding regions; (d) compare the measurement with a corresponding stored threshold value; and (e) operate the transducer based at least in part on the comparison. In one implementation, the controller is configured to operate the transducer by adjusting a transmitting power and/or a sonication pattern associated with the transducer. In addition, the controller may be further configured to compute the acoustic response dose by integrating the acoustic response level over a predetermined time period.

In some embodiments, the controller is further configured to cause a detection device and/or the transducer to measure acoustic signals from the target BBB region(s) and/or the surrounding regions; and determine the acoustic response level, the acoustic response dose, and/or the tissue response dose based at least in part on the measured acoustic signals. In addition, the system may further include one or more filters for filtering the measured acoustic signals from the target BBB region(s) and/or the surrounding regions. The filter(s) may be configured to select a harmonic and/or a sub-harmonic response to the transmitted ultrasound pulse. Alternatively, the filter(s) may be configured to select a broadband response to the transmitted ultrasound pulse.

In one embodiment, the controller is further configured to cause generation of microbubbles in the target BBB region(s) and/or the surrounding regions using the transducer. Additionally or alternatively, the system may include an administration device for introducing microbubbles into the target BBB region(s) and/or the surrounding regions. In one implementation, the administration device introduces a seed microbubble into the target BBB region(s) and/or the surrounding regions; the controller is then configured to cause generation of additional microbubbles using the seed microbubble and the transducer.

In various embodiments, the controller is further configured to determine the threshold values of the acoustic response level, the cumulative acoustic response dose and/or the tissue response dose associated with the target BBB region(s) and/or the surrounding regions based at least in part on anatomical characteristics thereof. In one embodiment, the system includes an imaging device for acquiring the anatomical characteristics of the target BBB region and its surrounding regions. For example, the image device may acquire images of the target BBB region(s) and/or the surrounding regions; the controller is further configured to determine the tissue response dose based at least in part on the acquired images.

There may be multiple target BBB regions and the controller may be further configured to determine and store the threshold values of the acoustic response level, the cumulative acoustic response dose and/or the tissue response dose associated with each of the target BBB regions and each of their surrounding regions. In some embodiments, the threshold values of the acoustic response level, the cumulative acoustic response dose and/or the tissue response dose associated with the target BBB region(s) are different from the threshold values of the acoustic response level, the cumulative acoustic response dose and/or the tissue response dose associated with the surrounding regions. In addition, the surrounding regions may include tissue having different types at different locations; the controller may be further configured to determine the threshold values of the acoustic response level, the cumulative acoustic response dose and/or the tissue response dose associated with each type of the tissue at each location of the surrounding regions.

The tissue response dose may include a temperature associated with the target BBB region(s) and/or the surrounding regions. In some embodiments, the tissue response dose is acquired by measuring an MRI $T_2$ relaxation time associated with the target BBB region(s) and/or the surrounding regions. In addition, the tissue response dose may include information derived from MRI $T_2^*$ imaging and/or MRI $T_2^*$ weighted imaging associated with the target BBB region(s) and/or the surrounding regions. Further, the controller may be configured to determine whether the acoustic response level, the acoustic response dose, and/or the tissue response dose exceeds the corresponding threshold value; and if so, suspend ultrasound sonication, and if not, cause the transducer to transmit a second ultrasound pulse.

In another aspect, the invention relates to a method of applying ultrasound sonication from a transducer to temporarily disrupt a patient's BBB. In various embodiments, the method includes (a) storing one or more threshold values of an acoustic response level, an acoustic response dose and/or a tissue response dose associated with one or more target BBB regions and their surrounding regions based on anatomical characteristics thereof; (b) causing the transducer to transmit one or more ultrasound pulses; (c) acquiring the acoustic response level, the acoustic response dose, and/or the tissue response dose associated with the target BBB region(s) and/or the surrounding regions; (d) comparing the measurement with a corresponding stored threshold value; and (e) operating the transducer based at least in part on the comparison. For example, operating the transducer may include adjusting a transmission power and/or a pulse pattern associated with the transducer. In one implementation, the acoustic response dose includes an integral of the acoustic response level over a predetermined time period.

In some embodiments, the method further includes measuring acoustic signals from the target BBB region(s) and/or the surrounding regions; and determining the acoustic response level, the acoustic response dose, and/or the tissue response dose based at least in part on the measured acoustic signals. In addition, the method may include filtering the measured acoustic signals using one or more filters. For example, the filter(s) may select a harmonic and/or a sub-harmonic response to the transmitted ultrasound pulse. Alternatively, the filter(s) may select a broadband response to the transmitted ultrasound pulse.

In some embodiments, the method further includes introducing microbubbles into the target BBB region(s) and/or the surrounding regions. The microbubbles may be introduced by activating the transducer to transmit the second pulse and/or using an administration device. In one embodiment, the administration device injects a seed microbubble into the target BBB region(s) and/or its surrounding regions, and the microbubbles are generated using the seed microbubble and the transducer.

In various embodiments, the threshold values of the acoustic response level, the cumulative acoustic response dose and/or the tissue response dose associated with the target BBB region(s) and the surrounding regions are determined based at least in part on anatomical characteristics thereof. In one embodiment, the method further includes acquiring images of the target BBB region(s) and/or the surrounding regions; the anatomical characteristics are then determined based at least in part on the acquired images.

There may be multiple target BBB regions; the method may further include determining and storing the threshold values of the acoustic response level, the cumulative acoustic response dose and/or the tissue response dose associated with each of the target BBB regions and each of their surrounding regions. In addition, the threshold values of the acoustic response level, the cumulative acoustic response dose and/or the tissue response dose associated with the target BBB region may be different from the threshold values of the acoustic response level, the cumulative acoustic response dose and/or the tissue response dose associated with the surrounding regions. In some embodiments, the surrounding regions include tissue having different types at different locations; the method further includes determining the threshold values of the acoustic response level, the cumulative acoustic response dose and/or the tissue response dose associated with each type and/or each location of the tissue in the surrounding regions.

The tissue response dose may include a temperature associated with the target BBB region(s) and the surrounding regions. In some embodiments, the tissue response dose is acquired by measuring an MRI $T_2$ relaxation time associated with the target BBB region(s) and/or the surrounding regions. In addition, the tissue response dose may include information derived from MRI $T_2^*$ imaging and/or MRI $T_2^*$ weighted imaging associated with the target BBB region(s) or the surrounding regions. In one embodiment, the method further includes determining whether the acoustic response level, the acoustic response dose, and/or the tissue response dose exceeds the corresponding threshold value; and if so, suspending the ultrasound sonication, and if not, causing the transducer to transmit a second ultrasound pulse.

Still another aspect of the invention relates to a method of applying a therapeutic agent to a brain tumor. In various embodiments, the method includes (a) storing one or more threshold values of an acoustic response level, an acoustic response dose and/or a tissue response dose associated with one or more target BBB regions and/or their surrounding regions based on anatomical characteristics thereof; (b) transmitting, using a phased array of transducers, one or more ultrasound pulses converging at a focus that includes the target BBB regions; (c) acquiring the acoustic response level, the acoustic response dose, and/or the tissue response dose associated with the target BBB region(s) or their surrounding regions; (d) comparing the measurement with a corresponding stored threshold value; (e) operating the transducer array based at least in part on the comparison; and (f) administering the therapeutic agent to the target BBB region. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U.

As used herein, the term "substantially" means ±10 seconds, and in some embodiments, ±5 seconds. "Clinically tolerable" means having an undesired (and sometimes the lack of a desired) effect on tissue that is considered insignificant by clinicians, e.g., prior to triggering the onset of damage thereto. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention in conjunction with the drawings, wherein.

DETAILED DESCRIPTION

Figure 1:
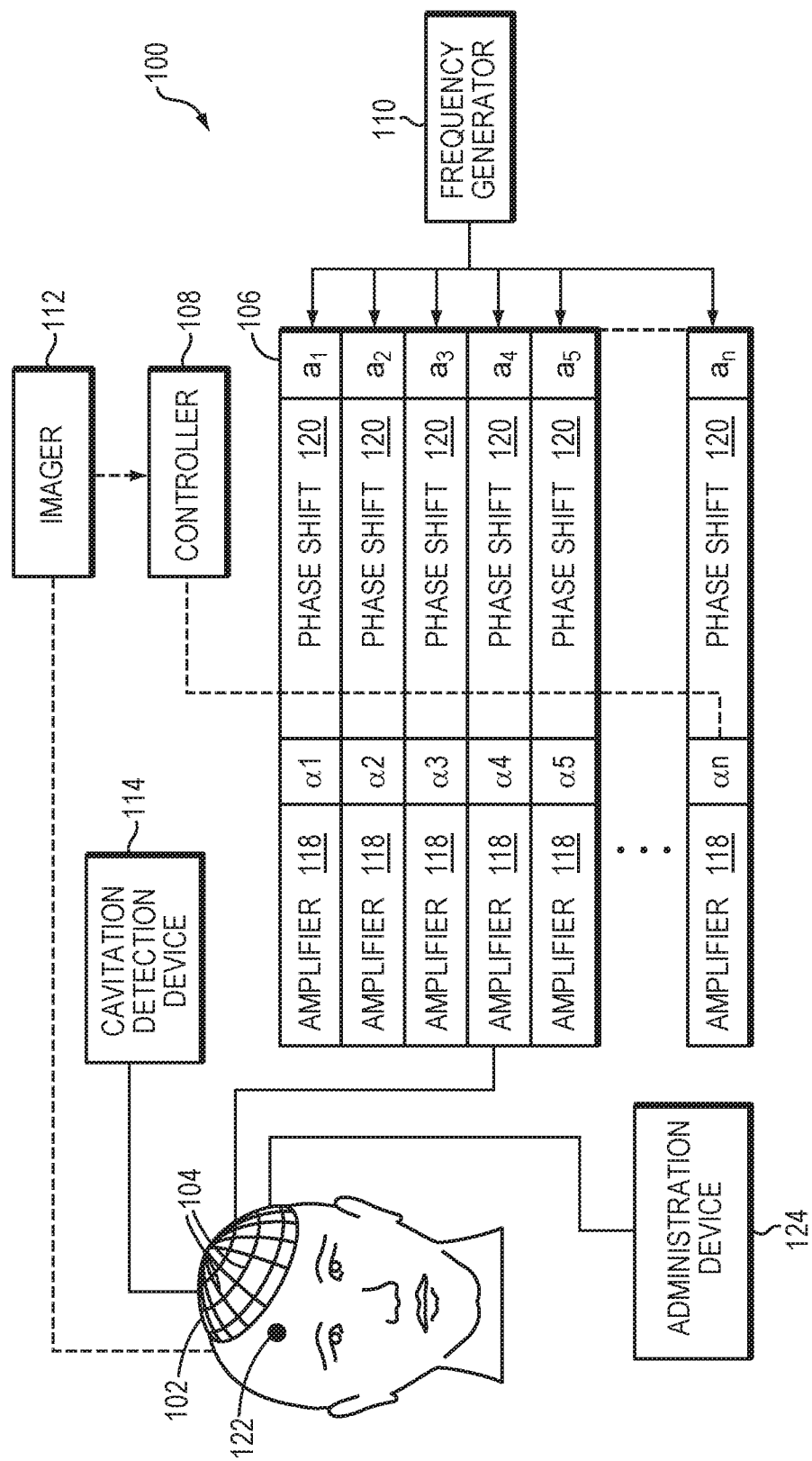
FIG. 1 schematically depicts an exemplary ultrasound system in accordance with various embodiments of the current invention.

FIG. 1 illustrates an exemplary ultrasound system 100 for focusing ultrasound within a patient's brain (e.g., a target BBB region) through the skull. The applied ultrasound sonication may induce microbubble cavitation and disrupt the target BBB region in a controlled and reversible manner. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics of the skull, the target BBB region and the tissue surrounding the BBB region. The ultrasound system 100 and/or imager 112 may be utilized to detect the presence, type, and/or location associated with microbubble cavitation as further described below. Additionally or alternatively, in some embodiments, the system further includes a cavitation detection device (such as a hydrophone or suitable alternative) 114 to detect information associated with microbubble cavitation.

The array 102 may have a curved (e.g., spherical or parabolic) shape suitable for placing it on the surface of the skull, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the patient's skull onto a selected region 122 of the patient's BBB, and account for wave distortions induced in the skull and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns. In certain embodiments, the computation is based on detailed information about the characteristics (e.g., structure, thickness, density, etc.) of the intervening tissue (e.g., the skull and/or brain tissue) located between the transducer elements and the selected region 122 and their effects on propagation of acoustic energy. Such information may be obtained from the imager 112. Image acquisition may be three-dimensional or, alternatively, the imager 112 may provide a set of two-dimensional images suitable for reconstructing a three-dimensional image of the skull from which thicknesses and densities can be inferred. Image-manipulation functionality may be implemented in the imager 112, in the controller 108, or in a separate device.

Figure 2A:
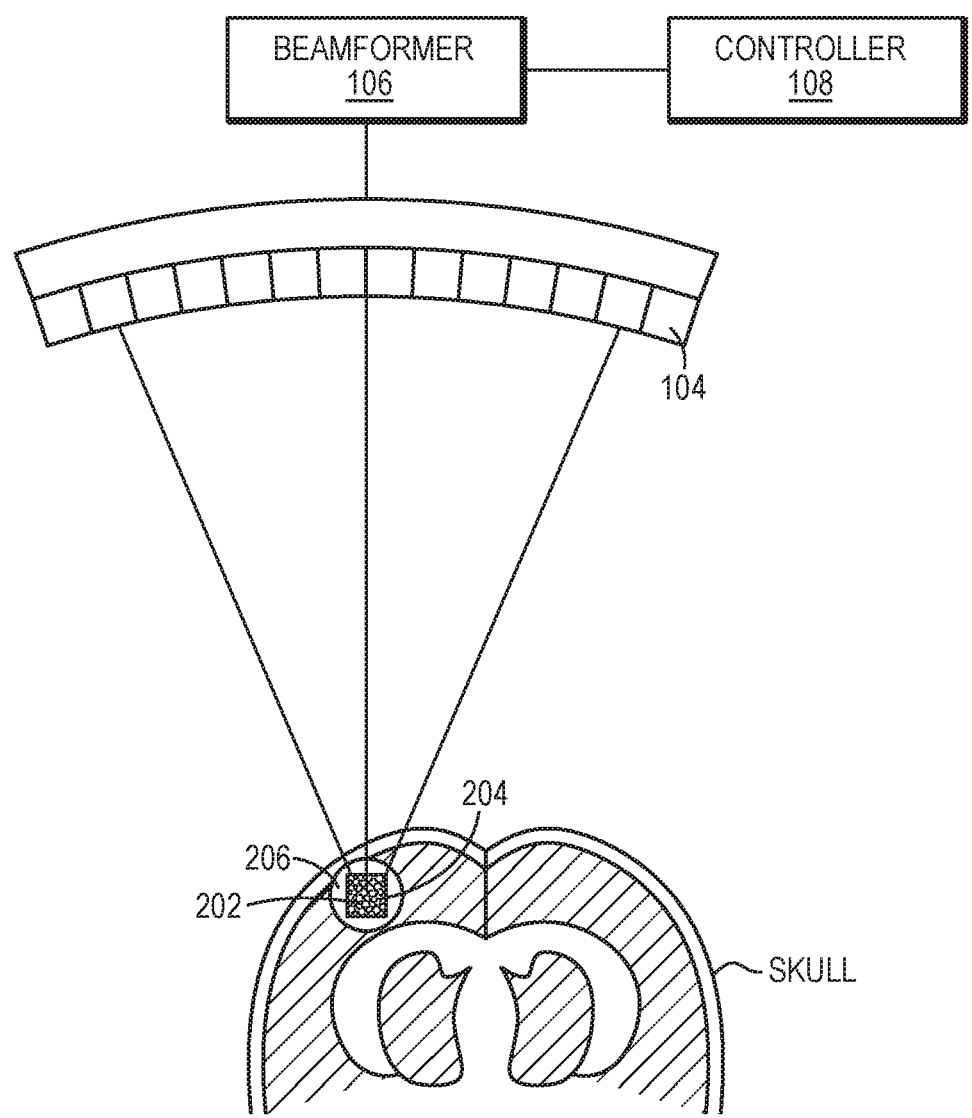
FIG. 2A depicts presence of microbubbles in a target tissue region in accordance with various embodiments.

Referring to FIG. 2A, in various embodiments, the acoustic energy emitted by the transducer elements 104 may be above a threshold and thereby cause generation of a small cloud of gas bubbles (or "microbubbles") 202 in the liquid contained in the target BBB region 204. The microbubbles 202 can be formed due to the negative pressure produced by the propagating ultrasonic waves or pulses, when the heated liquid ruptures and is filled with gas/vapor, or when a mild acoustic field is applied on tissue containing cavitation nuclei. Generally, at a relatively low acoustic power (e.g., 1-2 Watts above the microbubble-generation threshold), however, the generated microbubbles 202 undergo oscillation with compression and rarefaction that are equal in magnitude and thus the microbubbles generally remain unruptured. At a higher acoustic power (e.g., more than 10 Watts above the microbubble-generation threshold), the generated microbubbles 202 undergo rarefaction that is greater than compression, which may cause cavitation of the microbubbles. The microbubble cavitation may result in transient disruption (or "opening") of the targeted BBB region 204, thereby allowing therapeutic or prophylactic agents present in the bloodstream to penetrate the "opened" BBB region 204 and effectively deliver therapy to the targeted brain cells.

Referring again to FIG. 1, in some embodiments, microbubbles are introduced into the patient's bloodstream, and may either be injected systemically into the patient's brain or locally into the target BBB region 204 using an administration system 124. For example, the microbubbles may be introduced into the patient's brain in the form of liquid droplets that subsequently vaporize, as gas-filled bubbles, or entrained with another suitable substance, such as a conventional ultrasound contrast agent. The injected microbubbles may themselves create or facilitate the creation of additional microbubbles. Therefore, the actual effect on the tissue may result from a combination of the injected microbubbles and microbubbles additionally created in the tissue. Approaches to generating the microbubbles and/or introducing the microbubbles to the target region are provided, for example, in U.S. patent application Nos. and 62/366,200, 62/597,071, Ser. Nos. 15/708,214, 15/837,392 and 62/597,073, the contents of which are incorporated herein by reference.

Figure 2B:
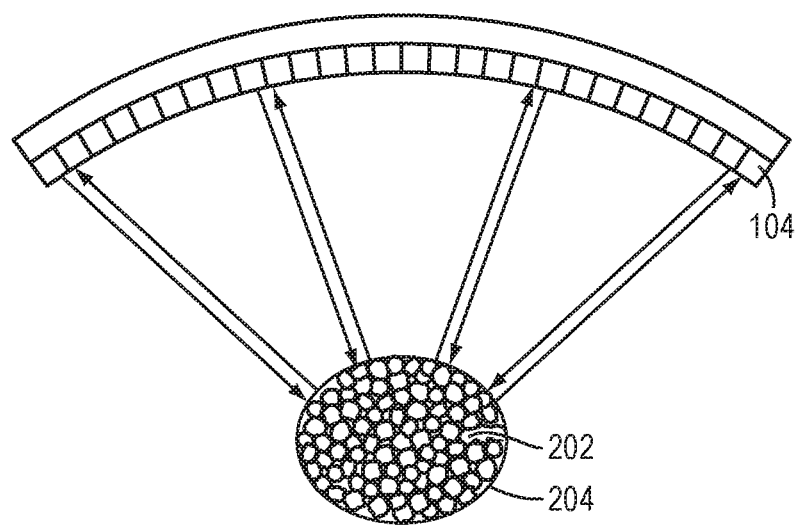
FIGS. 2B-2D depict various configurations of the transducer elements performing a cavitation-detecting approach in accordance with various embodiments.
Figure 2C:
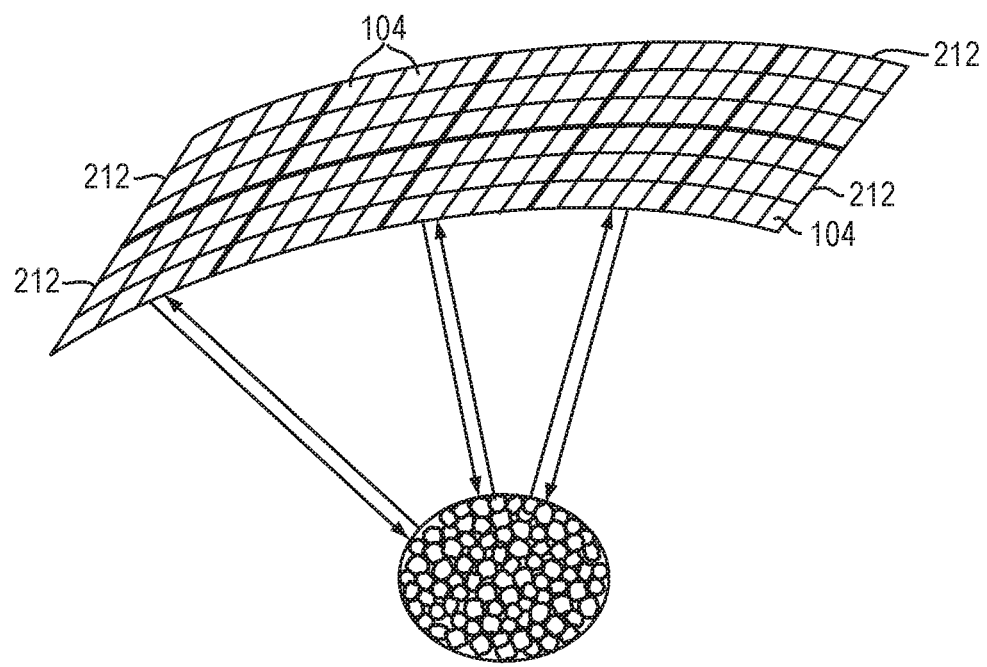
Figure 2D:
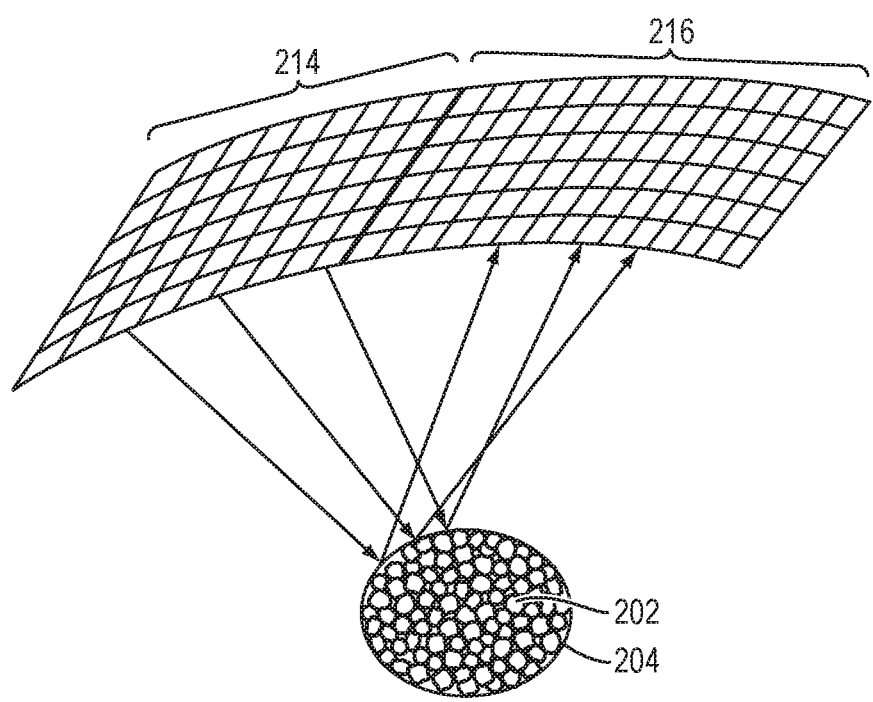

To avoid undesired damage of the target BBB region 204 and/or its surrounding tissue 206 resulting from the microbubble cavitation, in various embodiments, the formation and/or amount of induced microbubbles 202 in the target BBB region 204 is monitored by detecting acoustic signals emanating therefrom using the cavitation detection device 114, which then transmits the signals to the controller 108. Alternatively, the transducer elements 104 may possess both transmit and detect capabilities. Referring to FIG. 2B, in one embodiment, each individual transducer element 104 alternates between transmitting ultrasound signals to the microbubbles and receiving ultrasound signals therefrom. For example, all transducer elements 104 may substantially simultaneously transmit ultrasound to the microbubbles 202 and subsequently receive echo signals therefrom. Referring to FIG. 2C, in one implementation, the transducer array is divided into multiple sub-regions 212; each sub-region 212 comprises a one- or two-dimensional array (i.e., a row or a matrix) of transducer elements 104. The sub-regions 212 may be separately controllable, i.e., they are each capable of (i) emitting ultrasound waves/pulses at amplitudes, frequencies and/or phases that are independent of the amplitudes and/or phases of the other sub-regions 212, and (ii) measuring acoustic signals from the microbubbles 202. In one embodiment, the sub-regions 212 are assigned different amplitudes, frequencies and/or phases from one another, and activated, one at a time, to transmit ultrasound to and receive echo signals from the microbubbles 202. Referring to FIG.

2D, in another embodiment, the transducer array is divided into a transmit region 214 and a receive region 216; transducer elements in the transmit region 214 transmit the ultrasound waves/pulses while transducer elements in the receive region 216 receive the echo signals from the microbubbles 202. The received signals are then transmitted to the controller 108 for analysis. The transmit region 214 and receive region 216 of the transducer array may be configured in different patterns and shapes at various locations of the transducer array.

Figure 3A:
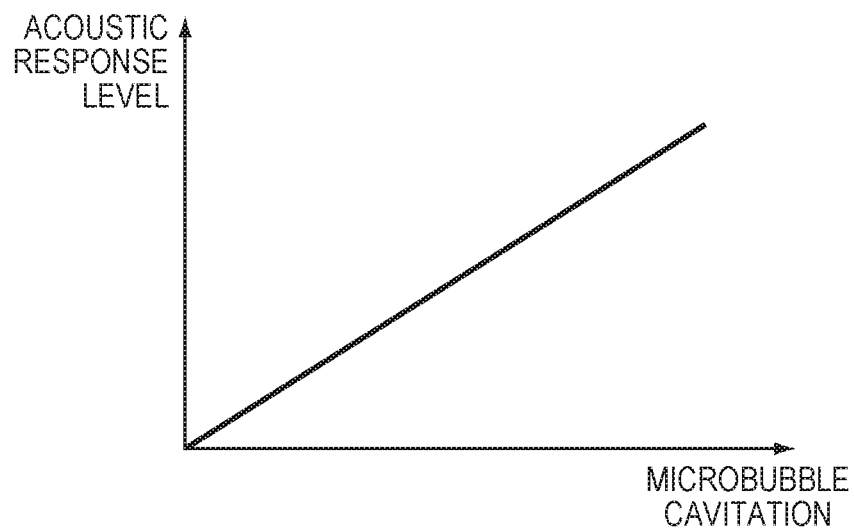
FIGS. 3A and 3B depict various relationships between an amplitude of a detected acoustic response level and a magnitude of the microbubble cavitation in accordance with various embodiments.
Figure 3B:
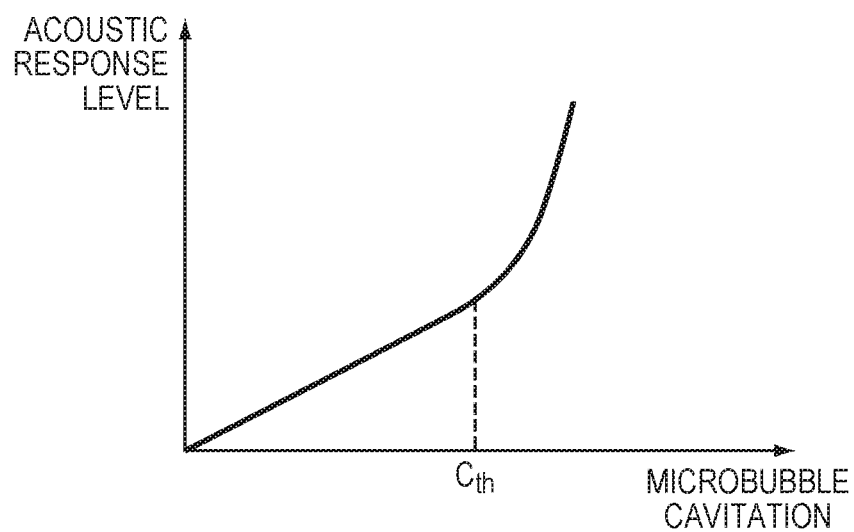

The microbubble acoustic signals may be emissions resulting from the shape change of the microbubbles 202 and/or reflections resulting from the microbubble encapsulating gas. The acoustic signals may include (i) an instantaneous acoustic response level and/or (ii) a spectral distribution of the acoustic response. The acoustic response level corresponds, either linearly or nonlinearly but in a known manner, to the magnitude of the acoustically driven cavitation. For example, referring to FIG. 3A, the amplitude of the detected acoustic response level may linearly correlate to the magnitude of the microbubble cavitation through the entire range thereof. Alternatively, referring to FIG. 3B, the linear correlation may occur only when the magnitude of the microbubble cavitation is below a threshold cavitation, $C_{th}$. When the magnitude of the cavitation exceeds the threshold, $C_{th}$, a small increase of the cavitation may result in a large increase of the response level of the acoustic signals.

The relationship between the amplitude of the acoustic response level and the magnitude of the microbubble cavitation may be empirically established from a pre-clinical study, a pre-treatment procedure, and/or from known literature. For example, in a pre-clinical study, the imager 112 may directly image the amount and/or area associated with the microbubble cavitation events, and based thereon, the magnitude of the microbubble cavitation may be quantified. Substantially simultaneously, the acoustic signals from the microbubble cavitation can be detected by the cavitation detection device 114 and/or transducer array 102 and subsequently analyzed by the controller 108 to acquire the amplitudes associated therewith. A relationship between the quantified magnitude of the microbubble cavitation and the amplitude of the acoustic response level can then be established.

In addition, the acoustic signals may include a spectral distribution of the acoustic response that indicates the type and/or location of the microbubble cavitation. This is because each type of the cavitation at each location may have its own spectral "signature" that represents the unique nonlinear response of the microbubbles. For example, the acoustic response of microbubbles may be linear at a relatively low acoustic power (e.g., 1-2 Watts above the microbubble-generation threshold); the spectral distribution of the detected signals may thus include a frequency that is the same as or a harmonic of that of the incident ultrasound waves (i.e., the fundamental frequency or a base harmonic frequency). If stable cavitation is induced at an intermediate acoustic power (e.g., 5 Watts above the microbubble-generation threshold), the spectral distribution of the detected signals may include a strong sub-harmonic response (i.e., having more components at the sub-harmonic frequencies and/or having larger amplitudes of the sub-harmonic frequencies). Likewise, if inertial cavitation is induced at a high acoustic power (e.g., 10 Watts above the microbubble-generation threshold), the detected signals may include a broadband response. Thus, by detecting and analyzing the acoustic signals emitted from the microbubbles, the presence, type and/or of cavitation induced in tissue during an ultrasound procedure can be determined. Approaches to monitoring the cavitation events using signals from the microbubbles are provided, for example, in U.S. patent application Ser. No. 15/415,351, and the content of which is incorporated herein by reference.

In various embodiments, the detected spectral distribution of the acoustic response is filtered by one or more suitable filters implemented in hardware and/or software. For example, the filters may include multiple bandpass filters and/or window functions, each associated with a frequency component (e.g., the base harmonic frequency or sub-harmonic frequency) of the spectral signature. In one embodiment, the filters include a baseband filter that allows the baseband response of the signals to be processed. The filters may thus advantageously improve the resolution and/or signal-to-noise ratio of the detected signals, thereby allowing the presence, type and/or location of the microbubble cavitation to be reliably and accurately determined. Suitable filters are well-known in the art of signal processing (in particular, digital signal processing) and readily implemented without undue experimentation.

Alternatively or additionally, the microbubble cavitation may be monitored using a cumulative acoustic response dose value that corresponds, either linearly or nonlinearly, to the cumulative cavitation-related acoustic energy delivered via the microbubbles over an entire sonication or over multiple successive sonication pulses. This is because the tissue tolerance may be a function both of the instantaneous response level and the cumulative response dose. For example, even if an instantaneous response level is below its corresponding predetermined threshold, the cumulative response dose may exceed its predetermined threshold; this may result in permanent effects or damage to the target BBB region or its surrounding tissue. Conversely, even if the cumulative response dose is below its predetermined threshold, a burst instantaneous response level above the threshold may be clinically intolerable. Accordingly, in a preferred embodiment, both the instantaneous response level and cumulative response dose are monitored during the ultrasound procedure.

Figure 3C:
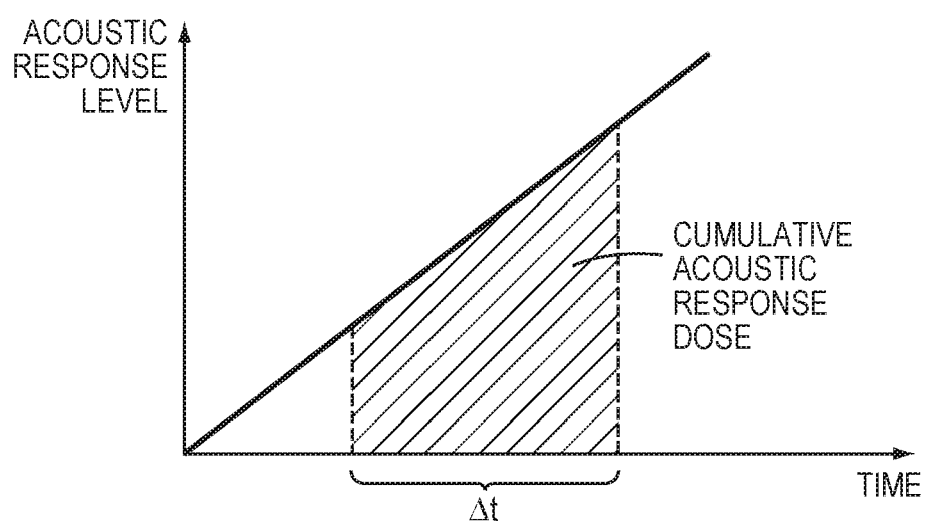
FIG. 3C depicts an exemplary relationship between a temporal acoustic response level and a cumulative acoustic response dose in accordance with various embodiments.

In some embodiments, the cumulative acoustic response dose is defined utilizing the instantaneous acoustic response level. For example, referring to FIG. 3C, the cumulative acoustic response dose may be an integral of the acoustic response level over a predetermined time period, $\Delta t$; the predetermined time period may be the entire sonication procedure or over one or more successive sonication pulses. Accordingly, based on the received acoustic signals during the ultrasound procedure, the controller 108 may compute the acoustic response dose during any desired time period.

Figure 4A:
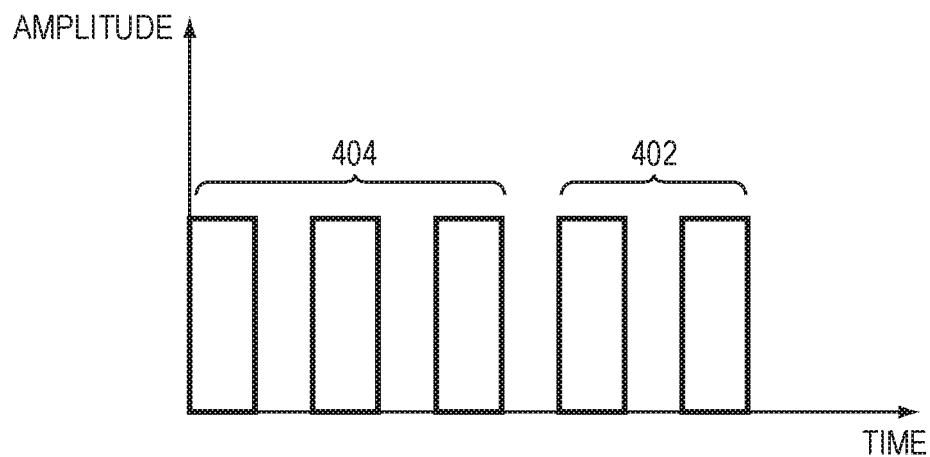
FIGS. 4A-4C illustrate amplitude variations of ultrasound pulses during an ultrasound procedure in accordance with various embodiments.
Figure 4B:
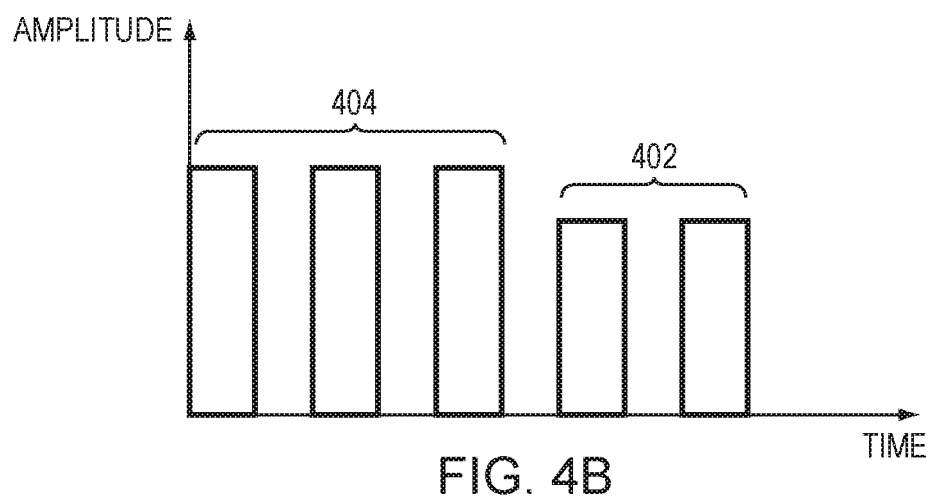
Figure 4C:
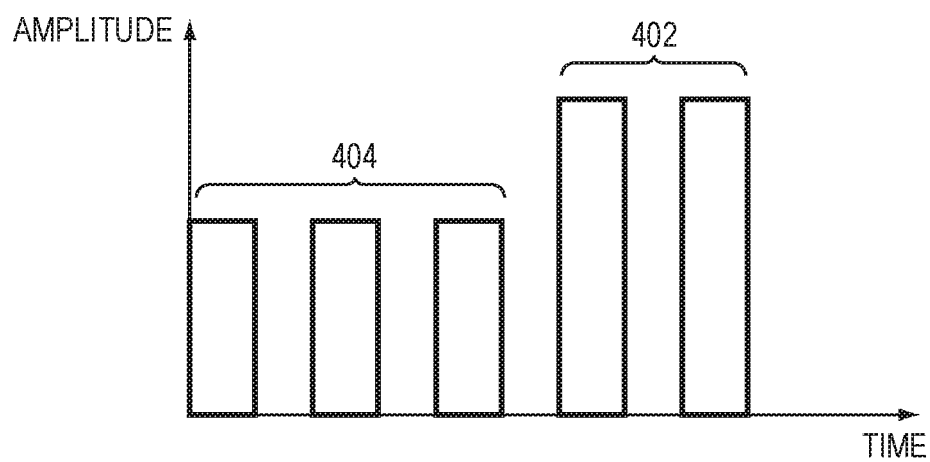
Figure 4D:
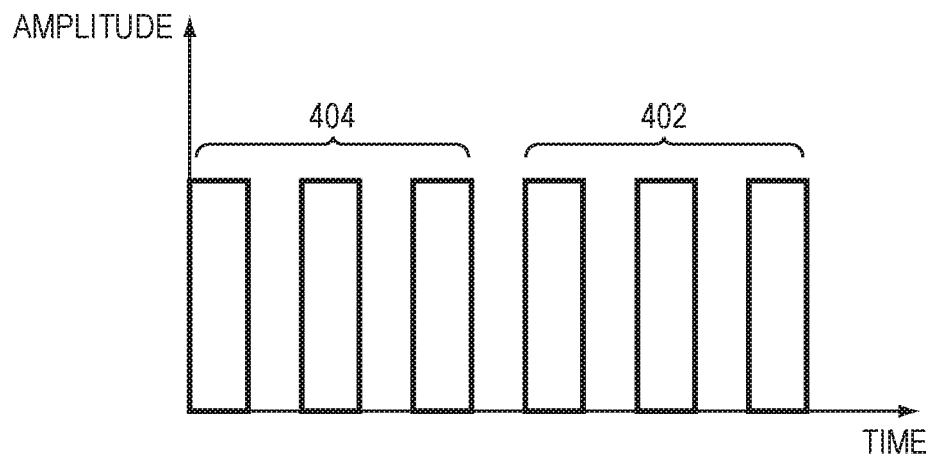
FIGS. 4D-4F illustrate various sonication patterns applied during an ultrasound procedure in accordance with various embodiments.
Figure 4E:
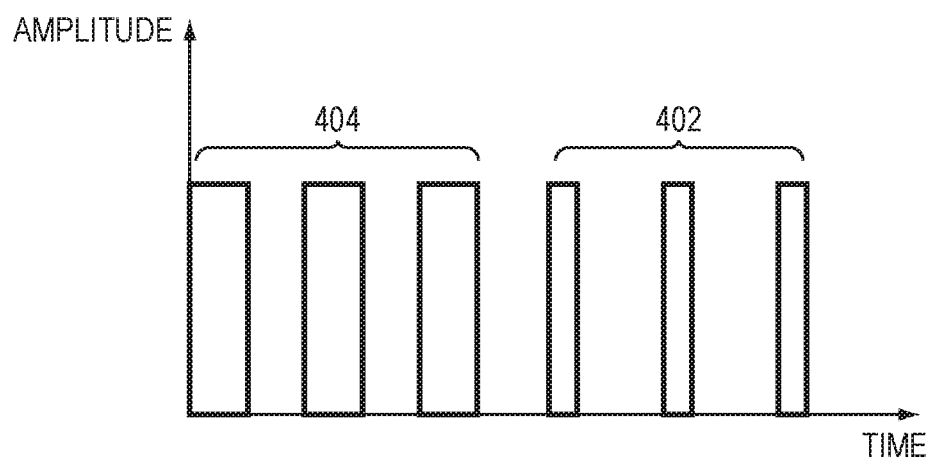
Figure 4F:
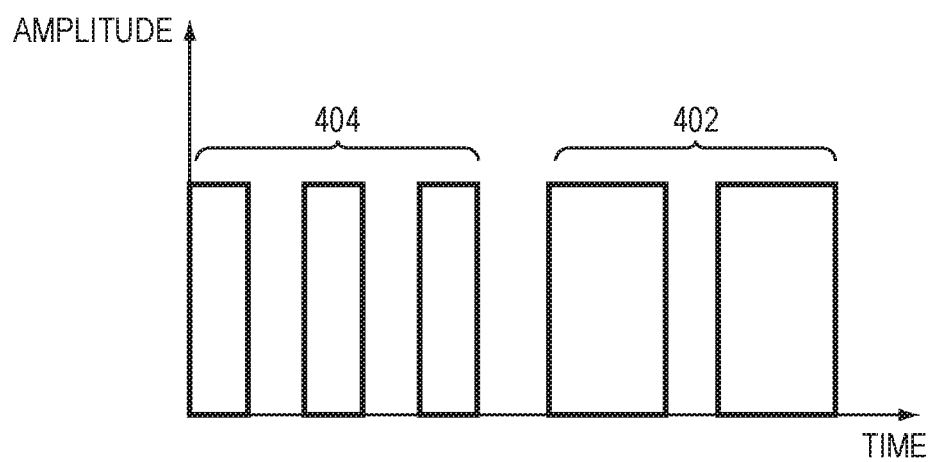

In addition, the detected acoustic response level and/or computed acoustic response dose may be compared with their associated predetermined threshold values stored in a databased in memory; the threshold values represent an upper limit of the magnitude and/or amount of the microbubble cavitation that can be clinically tolerated. If the acoustic response level and/or acoustic response dose is at or above the predetermined threshold value, the ultrasound procedure may be suspended to avoid inducing more microbubble cavitation, thereby avoiding damage to the target and/or non-target tissue regions. If, however, the acoustic response level and/or acoustic response dose is below the corresponding predetermined threshold value, the ultrasound transducer elements 104 may deliver additional acoustic energy to the microbubbles so as to induce additional cavitation to disrupt the target BBB region. For example, referring to FIGS. 4A-4C, the transducer elements 104 may be activated to transmit one or more additional pulses 402 to the microbubbles; the amplitude of the additional pulse(s) 402 may be the same or different from that of the previous pulses 404. Alternatively or additionally, the sonication pattern (e.g., a frequency, a focusing shape, and/or a sonication profile varying with time) of the additional pulses 402 may be the same or different from that of the previous pulses 404. For example, a duty cycle of the elements' activation time in the additional pulses 402 may be the same, smaller than or larger than that in the previous pulses 404 as depicted in FIGS. 4D-4F. Generally, the duty cycles positively correlate to energy levels delivered to the microbubbles—a higher duty cycle corresponds to larger energy, because the power is on for most of the time.

In some embodiments, when the acoustic response level and/or acoustic response dose is below the corresponding predetermined threshold value, additional microbubbles may be generated and/or introduced into the target BBB region in order to induce further microbubble cavitation. This can be achieved by activating the transducer array 102 to deliver more acoustic energy to the target BBB region and/or activating the administration system 124 to inject additional microbubbles into the target BBB region. In some embodiments, the administration device 124 first injects a seed microbubble into the target BBB region; the transducer array 102 then transmits an acoustic energy to the seed microbubble so as to generate more microbubbles.

The threshold values of the acoustic response level and cumulative acoustic response dose may be determined based on the tissue types, properties and/or other anatomical characteristics of the target BBB region and/or its surrounding region—the target BBB region and/or its surrounding region may include different types of tissue and/or have different tissue properties (e.g., densities, tolerance of thermal energy, thermal absorption coefficients, etc.) and thereby respond differently to the ultrasound pulses and/or microbubble cavitation; consequently, thresholds of the acoustic response level and acoustic response dose may differ for different types of tissue at different locations. In addition, the threshold values of the acoustic response level and cumulative acoustic response dose may depend on other parameters associated with an ultrasound treatment protocol, sonication pattern (e.g., the frequency, duty cycle, focusing shape, and/or sonication profile varying with time) and/or history of the acoustic and/or tissue response during the current or previous treatments. For example, lower threshold values may be used for ultrasound pulses that have a higher duty cycle; this is because the target/non-target tissue may have less time to relax between consecutive pulses. In some embodiments, larger threshold values are tolerable at the beginning of the treatment but smaller thresholds are preferred after, for example, the occurrence of a major therapeutic event during the treatment.

Figure 5A:
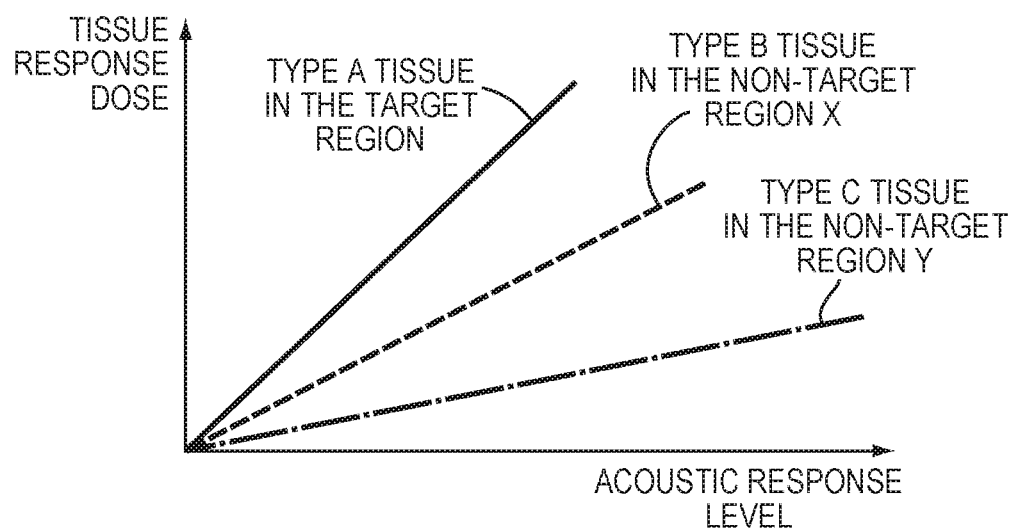
FIG. 5A depicts a relationship between a tissue response dose and a detected acoustic response level in accordance with various embodiments.

In various embodiments, operation of the transducer elements 104 (such as activation, deactivation or adjustment of the sonication pattern) and/or the administration system 124 is determined based on a tissue response dose. The tissue response dose may be based on the maximum clinically tolerable temperature for each affected target/non-target region based on the types, properties and/or other anatomical characteristics of the tissue in each region. Thus, various type of tissue having different properties at different locations may have different tissue response doses. The tissue response dose may be obtained using any suitable approach prior to and/or during treatment. For example, referring to FIG. 5A, the tissue response dose may be empirically correlated to the acoustic response level and/or cumulative acoustic response dose; accordingly, the tissue response dose may be acquired based on the acoustic response level and/or cumulative acoustic response dose detected/computed as described above.

Figure 5B:
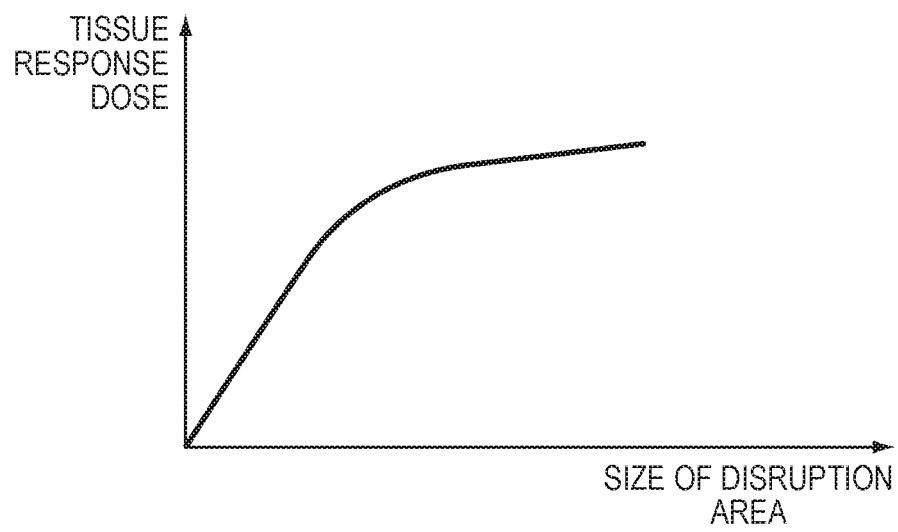
FIG. 5B depicts a relationship between a tissue response dose and a size of the target/non-target region disrupted by the microbubble cavitation in accordance with various embodiments.

Additionally or alternatively, the tissue response dose may be determined using the imager (e.g., an MRI device) 112. For example, the MRI device 112 may measure the disrupted area of the target BBB region 204 and/or its surrounding region 206 resulting from the microbubble cavitation in real time. The size of the disrupted area may correlate to the tissue response dose as shown in FIG. 5B. In various embodiments, the temperature at the target BBB region and/or it surrounding region represents the tissue response dose thereof. The temperature dependence of MRI $T_2$ relaxation times in the target BBB region 204 and its surrounding region 206 may be determined prior to the ultrasound procedure. During the ultrasound procedure, the MRI $T_2$ relaxation time can be measured quickly (within 1 ms to 1 sec) in order to estimate the temperature of the target BBB region 204 and/or it surrounding region 206 in real time. This approach advantageously provides real-time temperature feedback to the ultrasound controller 108 which may adjust the ultrasound transmission accordingly. For example, if the measured temperature is below the predetermined maximum temperature, the ultrasound procedure may continue to induce more microbubble cavitation to disrupt the target BBB region 204 by, for example, transmitting additional pulses, increasing the amplitudes and/or duty cycles of the pulses. If, however, the measured temperature is above the maximum temperature, the ultrasound procedure may be halted to avoid permanently damaging the tissue. It should be noted that other MRI signals may be additionally or alternatively used to estimate the tissue response of the target BBB region 204 and/or it surrounding region 206. For example, MRI $T_2^*$ weighted imaging may advantageously detect an extravasation (level) of the blood in the brain. In addition, temperature-sensitive MR parameters, such as the proton resonance frequency (PRF), the diffusion coefficient (D), $T_1$ and $T_2$ relaxation times, magnetization transfer, and/or the proton density, as well as temperature-sensitive contrast agents, may be utilized alone or in combination to estimate the tissue response.

Figure 6:
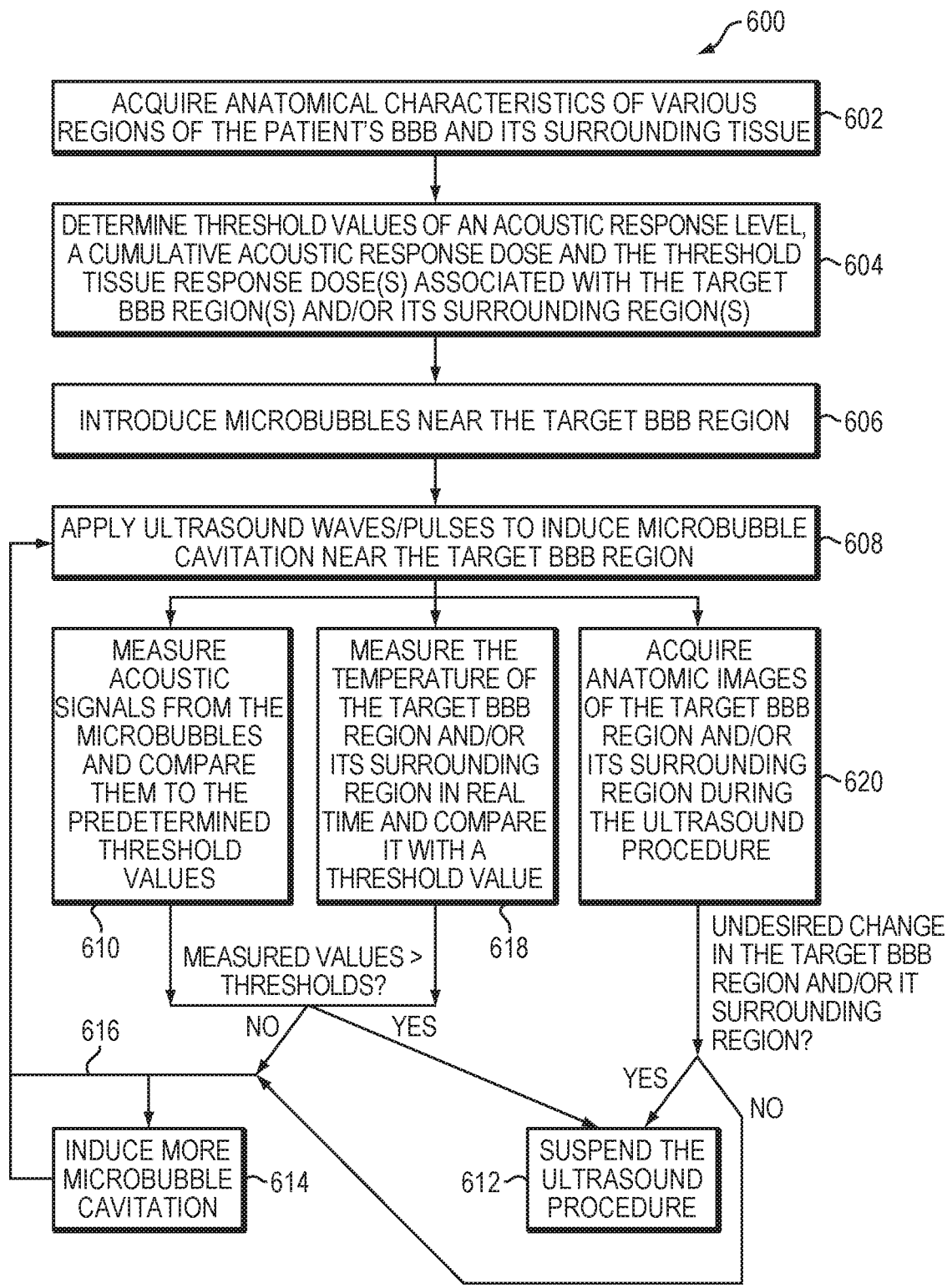
FIG. 6 is a flow chart illustrating an approach of using ultrasound sonication and microbubbles to temporarily disrupt a patient's BBB in accordance with some embodiments of the present invention.

FIG. 6 illustrates a representative approach 600 to using ultrasound sonication to induce microbubble cavitation for temporarily disrupting a patient's BBB in a controlled and reversible manner. In a first step 602, an imager (e.g., an MRI device) is utilized to acquire anatomical characteristics of various regions of the patient's BBB and its surrounding tissue prior to applying the ultrasound sonication. In a second step 604, threshold values of an acoustic response level and a cumulative acoustic response dose associated with the microbubbles at each one of the target BBB regions and/or its surrounding region(s), and threshold tissue response dose(s) associated with the target BBB region(s) and/or its surrounding region(s) may be determined based on the anatomical characteristics of the tissue extracted from the MRI data as described above. Different types of the target/non-target tissue at different locations may have different threshold values. The threshold values of the acoustic response level and cumulative acoustic response dose and the threshold tissue response dose(s) may then be stored in a database in memory that can be accessed by the controller 108. In a third step 606, microbubbles are generated by application of the ultrasound pulses and/or introduced by an administration system near the target BBB region. In a fourth step 608, the ultrasound transducer array may be activated to apply waves or pulses so as to induce microbubble cavitation near the target BBB region. In a fifth step 610, acoustic signals from the microbubbles may be continuously measured (e.g., after delivery of each sonication) and compared to the predetermined threshold values of the acoustic response level and/or cumulative acoustic response dose. If the amplitudes of the detected acoustic signals are above the threshold values, the magnitude and/or amount of microbubble cavitation may exceed a safe (i.e., clinically tolerable) level; therefore, the ultrasound procedure may be suspended until the detected acoustic signal amplitudes fall below the threshold values or after a recovery interval following application of the maximum tolerable dose (in a sixth step 612).

If the acoustic response level and/or cumulative acoustic response dose are below the respective threshold values, more microbubbles may be generated and/or introduced to increase cavitation events to continue disruption of the target BBB region (in a seventh step 614). Additionally or alternatively, the ultrasound transducer may be activated to deliver the next wave/pulse with the same or different amplitude and sonication pattern from the previous applied waves/pulses (in an eighth step 616). In addition, during the ultrasound procedure, the imager (e.g., MRI device) may measure the temperature of the target BBB region and/or its surrounding region in real time (in a ninth step 618). For example, the real-time temperature may be acquired by measuring the MRI $T_2$ relaxation time. Again, if the measured temperature is below the predetermined threshold of the tissue response dose, additional microbubbles may be generated and/or introduced (step 614) and/or the ultrasound procedure may continue (step 616). If, however, the measured temperature is above the threshold, the ultrasound procedure is halted to avoid overheating which may result in permanent damage to the target BBB region and/or its surrounding region (step 612). In one embodiment, the database may alternatively or additionally store threshold values associated with other temperature sensitive MR parameters, such as the PRF, diffusion coefficient (D), $T_1$ relaxation time, magnetization transfer, proton density, as well as parameters associated with the temperature sensitive contrast agents. The imager may then measure these parameters during the ultrasound procedure; the measured values may then be compared against the stored threshold values and, based thereon, the controller 108 may operate the transducer array 102 and/or administrative system as described above.

In some embodiments, the MRI device also acquires anatomic images of the target BBB region and/or its surrounding region during the ultrasound procedure (in a tenth step 620). If an undesired change in the target BBB region and/or its surrounding region is observed, the ultrasound procedure may be stopped immediately. The undesired change may include, for example, the size of the disrupted BBB area being larger than the desired area and/or a portion of the non-target surrounding region being disrupted. Embodiments of the present invention thus employ a cavitation detection device (or an ultrasound transducer array) and an imaging device to monitor formation/generation of the microbubbles, the cavitation events, and tissue response in real-time during an ultrasound procedure; based on the monitored response, disruption of the target BBB region may then be facilitated in a controlled manner without permanently damaging the target BBB region and/or its surrounding region.

Thereafter, a therapeutic agent may penetrate from the bloodstream to the targeted brain cells via the opened BBB region. The therapeutic agent may include any drug that is suitable for treating a brain tumor. For example, for treating glioblastoma (GBM), the drug may include or consist of, e.g., one or more of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, Cytarabine (cytosine arabinoside, ara-C)/ara-U, etc.

Those skilled in the art can select a drug and a BBB opening regime optimized to enhance drug absorption across the BBB within patient safety constraints. In this regard, it is known that the BBB is actually already disrupted in the core of many tumors, allowing partial penetration of antitumor drugs; but the BBB is widely intact around the "brain adjacent to tumor" (BAT) region where invasive/escaping GBM cells can be found, and which cause tumor recurrence. Overcoming the BBB for better drug delivery within the tumor core and the BAT can be accomplished using ultrasound as described herein. The drugs employed have various degrees of toxicity and various penetration percentages through the BBB. An ideal drug has high cytotoxicity to the tumor and no BBB penetration (so that its absorption and cytotoxic effects can be confined to regions where the BBB is disrupted), low neurotoxicity (to avoid damage to the nervous system), and tolerable systemic toxicity (e.g., below a threshold) at the prescribed doses. The drug may be administered intravenously or, in some cases, by injection proximate to the tumor region.

Functionality for performing disruption of a target BBB region in a controlled and reversible manner as described above, whether integrated within the controller 108 of the ultrasound system 100, the imager 122 and/or the administration system 124 or provided by a separate external controller, may be structured in one or more modules implemented in hardware, software, or a combination of both. In addition, the imager 122 and/or the administration system 124 may be controlled by the controller 108 or other separate processor(s). For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel® 80x86 assembly language if it is configured to run on an IBM® PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for temporarily disrupting a patient's blood-brain barrier (BBB), the system comprising:
an ultrasound transducer; and
a controller configured to:
(a) store a threshold value of a cumulative acoustic response dose associated with at least one of a target BBB region or its surrounding regions, the threshold value corresponding to a maximum clinically tolerable cumulative amount of microbubble cavitation;
(b) cause the transducer to transmit at least one ultrasound pulse;
(c) acquire the cumulative acoustic response dose associated with the at least one of the target BBB region or its surrounding regions;
(d) compare the cumulative acoustic response dose acquired in step (c) with the stored threshold value; and
(e) suspend ultrasound sonication when the cumulative acoustic response dose acquired in step (c) exceeds the stored threshold value.

2. The system of claim 1, wherein the controller is further configured to:
cause the transducer to measure acoustic signals from the at least one of the target BBB region or its surrounding regions; and
determine the cumulative acoustic response dose based at least in part on the measured acoustic signals.

3. The system of claim 2, further comprising a filter for filtering the measured acoustic signals from the at least one of the target BBB region or its surrounding regions.

4. The system of claim 3, wherein the filter is configured to select at least one of a harmonic or a sub-harmonic response to the transmitted ultrasound pulse.

5. The system of claim 3, wherein the filter is configured to select a broadband response to the transmitted ultrasound pulse.

6. The system of claim 1, wherein the controller is further configured to compute the cumulative acoustic response dose by integrating an acoustic response level.

7. The system of claim 1, wherein the controller is further configured to cause generation of microbubbles in the at least one of the target BBB region or its surrounding regions using the transducer.

8. The system of claim 1, further comprising an administration device for introducing microbubbles into the at least one of the target BBB region or its surrounding regions.

9. The system of claim 1, further comprising an administration device for introducing a seed microbubble into the at least one of the target BBB region or its surrounding regions, wherein the controller is further configured to cause generation of additional microbubbles using the seed microbubble and the transducer.

10. The system of claim 1, wherein the controller is further configured to determine the threshold value of the cumulative acoustic response dose associated with the at least one target BBB region or its surrounding regions based at least in part on anatomical characteristics thereof.

11. The system of claim 10, wherein there are a plurality of target BBB regions and the controller is further configured to determine and store the threshold value of the cumulative acoustic response dose associated with each of the target BBB regions and each of their surrounding regions.

12. The system of claim 10, wherein the threshold value of the cumulative acoustic response dose associated with the at least one target BBB region is different from the threshold value of the cumulative acoustic response dose associated with the surrounding regions.

13. The system of claim 10, wherein the surrounding regions comprise tissue having different types at different locations, and the controller is further configured to determine the threshold value of the cumulative acoustic response dose associated with each type of the tissue at each location of the surrounding regions.

14. The system of claim 10, further comprising an imaging device for acquiring the anatomical characteristics of the target BBB region and its surrounding regions.

15. The system of claim 14, wherein the image device further acquires images of the at least one of the target BBB region or its surrounding regions and the controller is further configured to determine the tissue response dose based at least in part on the acquired images.

16. The system of claim 1, wherein the controller is configured to also store a tissue response dose comprising a temperature associated with the at least one of the target BBB region or its surrounding regions.

17. The system of claim 1, wherein the controller is configured to also store a tissue response dose acquired by measuring an MRI $T_2$ relaxation time associated with the at least one of the target BBB region or its surrounding regions.

18. The system of claim 1, wherein the controller is further configured to:
cause the transducer to transmit a second ultrasound pulse when the cumulative acoustic response dose acquired in step (c) does not exceed the stored threshold value.

19. The system of claim 1, wherein the controller is configured to also store a tissue response dose comprising information derived from at least one of MRI $T_2^*$ imaging or MM $T_2^*$ weighted imaging associated with the at least one of the target BBB region or its surrounding regions.

20. The system of claim 1, wherein the controller is further configured to adjust at least one of a transmitting power or a sonication pattern associated with the transducer when the cumulative acoustic response dose acquired in step (c) does not exceed the stored threshold value.

21. The system of claim 1, further comprising a detection device configured to measure acoustic signals from the at least one of the target BBB region or its surrounding regions.

22. A system for temporarily disrupting a patient's blood-brain barrier (BBB), the system comprising:
an ultrasound transducer; and
a controller configured to:
(a) store a first threshold value of a cumulative acoustic response dose associated with at least one of a target BBB region or its surrounding regions, the first threshold value corresponding to a maximum clinically tolerable cumulative amount of microbubble cavitation;
(b) store a second threshold value of an acoustic response value associated with the at least one of the target BBB region or its surrounding regions, the second threshold value corresponding to a maximum clinically tolerable magnitude of microbubble cavitation;
(c) during a sonication cycle, cause the transducer to transmit a plurality of ultrasound pulses;
(d) for each ultrasound pulse, acquire the acoustic response value associated with the at least one of the target BBB region or its surrounding regions, and compare the acquired acoustic response value with the second threshold value;
(e) during the sonication cycle, acquire the cumulative acoustic response dose associated with the at least one of the target BBB region or its surrounding regions, and compare the acquired cumulative acoustic response dose with the first threshold value; and
(f) suspend ultrasound sonication when the cumulative acoustic response dose acquired in step (e) exceeds the first threshold value or when the acoustic response value acquired in step (d) exceeds the second threshold value.

23. The system of claim 21, wherein the detection device comprises a hydrophone.

24. The system of claim 21, wherein the controller is further configured to:
cause at least one of the detection device or the transducer to measure acoustic signals from the at least one of the target BBB region or its surrounding regions.

25. The system of claim 24, further comprising a filter for filtering the measured acoustic signals from the at least one of the target BBB region or its surrounding regions.

26. The system of claim 25, wherein the filter is configured to select at least one of a harmonic or a sub-harmonic response to the transmitted ultrasound pulse.

27. The system of claim 25, wherein the filter is configured to set a broadband response to the transmitted ultrasound pulse.

* * * * *